(12) United States Patent
De Kock et al.

(10) Patent No.: US 7,935,711 B2
(45) Date of Patent: May 3, 2011

(54) HIV INHIBITING 2-(4-CYANOPHENYLAMINO) PYRIMIDINE OXIDE DERIVATIVES

(75) Inventors: Herman Augustinus De Kock, Arendonk (BE); Piet Tom Bert Paul Wigerinck, Terhagen (BE)

(73) Assignee: Tibotec Pharmaceuticals Ltd., Little Island Co Cork (IE)

( * ) Notice: Subject to any disclaimer, the term of this patent is extended or adjusted under 35 U.S.C. 154(b) by 535 days.

(21) Appl. No.: 11/814,958

(22) PCT Filed: Feb. 20, 2006

(86) PCT No.: PCT/EP2006/060115
§ 371 (c)(1), (2), (4) Date: Jul. 27, 2007

(87) PCT Pub. No.: WO2006/087387
PCT Pub. Date: Aug. 24, 2006

(65) Prior Publication Data
US 2008/0194602 A1      Aug. 14, 2008

(30) Foreign Application Priority Data

Feb. 18, 2005   (EP) .................................... 05101270

(51) Int. Cl.
C07D 239/48   (2006.01)
A61K 31/505   (2006.01)

(52) U.S. Cl. ........................................ 514/272; 544/321

(58) Field of Classification Search .................. 544/321; 514/272
See application file for complete search history.

(56) References Cited

U.S. PATENT DOCUMENTS

| | | | |
|---|---|---|---|
| 2008/0214588 A1 | 9/2008 | De Kock et al. | |
| 2008/0262007 A1 | 10/2008 | Guillemont et al. | |
| 2009/0124644 A1 | 5/2009 | Heeres et al. | |
| 2009/0181993 A1 | 7/2009 | Guillemont et al. | |
| 2010/0016317 A1 | 1/2010 | Guillemont et al. | |
| 2010/0121060 A1 | 5/2010 | De Kock et al. | |
| 2010/0168104 A1 | 7/2010 | Guillemont et al. | |
| 2010/0234375 A1 | 9/2010 | Guillemont et al. | |

FOREIGN PATENT DOCUMENTS

| | | |
|---|---|---|
| WO | WO 00/27825 | 5/2000 |
| WO | WO 2004/002410 A2 | 1/2004 |

OTHER PUBLICATIONS

International Search Report dated Jun. 22, 2006 for related International Application No. PCT/EP2006/060115.

*Primary Examiner* — Deepak Rao
(74) *Attorney, Agent, or Firm* — Patton Boggs LLP

(57) ABSTRACT

HIV replication inhibitors of formula (I) a pharmaceutically acceptable addition salt; or a stereochemically isomeric form thereof, wherein $R^1$ is halo; $R^2$ and $R^3$ each independently are $C_{1-6}$alkyl. Pharmaceutical compositions containing these compounds as active ingredient and processes for preparing these compounds and compositions.

3 Claims, No Drawings

HIV INHIBITING 2-(4-CYANOPHENYLAMINO) PYRIMIDINE OXIDE DERIVATIVES

CROSS REFERENCE TO RELATED APPLICATIONS

This application is a national stage application of Patent Application No. PCT/EP2006/060115, filed Feb. 20, 2006, which application claims priority from EPO Patent Application No. 05101270.6, filed Feb. 18, 2005, both of which are hereby incorporated by reference in their entirety.

The present invention is concerned with pyrimidine oxide derivatives having HIV (Human Immunodeficiency Virus) replication inhibiting properties, the preparation thereof and pharmaceutical compositions comprising these compounds.

Resistance of the HIV virus against currently available HIV drugs continues to be a major cause of therapy failure. This has led to the introduction of combination therapy of two or more anti-HIV agents usually having a different activity profile. Significant progress was made by the introduction of HAART therapy (Highly Active Anti-Retroviral Therapy), which has resulted in an important reduction of morbidity and mortality in HIV patient populations treated therewith. HAART involves various combinations of nucleoside reverse transcriptase inhibitors (NRTIs), non-nucleoside reverse transcriptase inhibitors (NNRTIs) and protease inhibitors (PIs). Current guidelines for antiretroviral therapy recommend such triple combination therapy regimen even for initial treatment. However, these multidrug therapies not always are effective and never completely eliminate HIV. It has been reported that half of the patients receiving anti-HIV combination therapy do not respond fully to the treatment, mainly because of resistance of the virus to one or more drugs used. Switching to alternative combinations usually provides temporary relief but any form of long-term treatment will fail at the end because of the development of multidrug resistance. Moreover, it has been shown that resistant virus is carried over to newly infected individuals, resulting in severely limited therapy options for these drug-naive patients.

Therefore, there is a continued need for new drug combinations that are effective against HIV. New types of HIV inhibitors, differing in chemical structure and activity profile are needed in these new combinations. Finding such new active ingredients therefore is a highly desirable goal to achieve.

The present invention provides a particular novel series of bisaryl substituted pyrimidine derivatives which may find use in HIV therapy, in particular as a new component of drug combinations. WO-00/27825 describes particular bisaryl substituted pyrimidines having HIV replication inhibiting properties. The compounds of the present invention behave superior in terms of HIV replication inhibiting properties and show improved capability to inhibit the replication of mutant strains, in particular strains which have become resistant to one or more known NNRTIs, which strains are referred to as drug or multidrug resistant HIV strains.

The present invention concerns compounds of formula

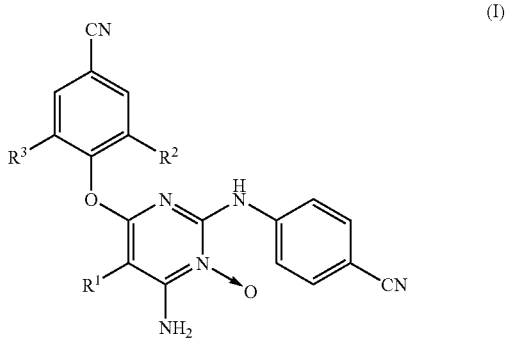

(I)

the pharmaceutically acceptable addition salts; or the stereochemically isomeric forms thereof, wherein
$R^1$ is halo;
$R^2$ and $R^3$ each independently are $C_{1-6}$alkyl.

As used herein the term "$C_{1-4}$alkyl" defines straight or branched chain saturated hydrocarbon radicals having from 1 to 4 carbon atoms such as methyl, ethyl, 1-propyl, 2-propyl, 1-butyl, 2-butyl, 2-methyl-1-propyl, and the like; "$C_{1-6}$alkyl" encompasses $C_{1-4}$alkyl radicals and the higher homologues thereof having 5 or 6 carbon atoms such as 1-pentyl, 2-pentyl, 3-pentyl, 1-hexyl, 2-hexyl, 2-methyl-1-butyl, 2-methyl-1-pentyl and the like. Of interest amongst $C_{1-6}$alkyl are the $C_{1-4}$alkyl radicals.

The term halo encompasses fluoro, chloro, bromo and iodo.

The compounds of this invention contain an N-oxide bond which may be represented by NO, by N=O, or by $N^+$—$O^-$ or, as used mostly in this specification and claims, by N→O.

For therapeutic use, salts of the compounds of formula (I) are those wherein the counter ion is pharmaceutically acceptable. However, salts which are non-pharmaceutically acceptable may also find use, for example, in the preparation or purification of a pharmaceutically acceptable compound. All salts, whether pharmaceutically acceptable or not are included within the ambit of the present invention.

The term "pharmaceutically acceptable addition salts" as used herein is meant to comprise the therapeutically active non-toxic acid addition salt forms, which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The compounds of formula (I) containing acidic protons may be converted into their therapeutically active non-toxic metal or amine addition salt forms by treatment with appropriate organic and inorganic bases.

The term addition salt also comprises the hydrates and solvent addition forms which the compounds of formula (I) are able to form. Examples of such forms are e.g. hydrates, alcoholates and the like.

Some of the compounds of formula (I) and their addition salts may contain one or more centers of chirality and exist as stereochemically isomeric forms. Stereoiosomers may exist where $R^2$ and $R^3$ are $C_{4-6}$alkyl. The term "stereochemically isomeric forms" as used herein defines all the possible stereoisomeric forms which the compounds of formula (I), and their addition salts may possess. Stereochemically isomeric forms of the compounds of formula (I) are intended to be embraced within the scope of this invention.

Preferred subgroups of compounds is those compounds of formula (I) as specified above, or any subgroup of compounds of formula (I) specified herein, wherein $R^1$ is chloro or bromo, more preferably wherein $R^1$ is bromo.

Other preferred subgroups of compounds is those compounds of formula (I) as specified above, or any subgroup of compounds of formula (I) specified herein, wherein $R^2$ and $R^3$ are $C_{1-4}$alkyl, more preferably wherein $R^2$ and $R^3$ are $C_{1-2}$alkyl, still more preferably wherein $R^2$ and $R^3$ are methyl.

Of particular interest are the compounds of formula (I) wherein $R^1$ is bromo and $R^2$ and $R^3$ are methyl.

In general, the compounds of formula (I) can be prepared by N-oxidizing the corresponding compounds of formula (II) using art-known procedures for converting a tertiary nitrogen into its N-oxide form.

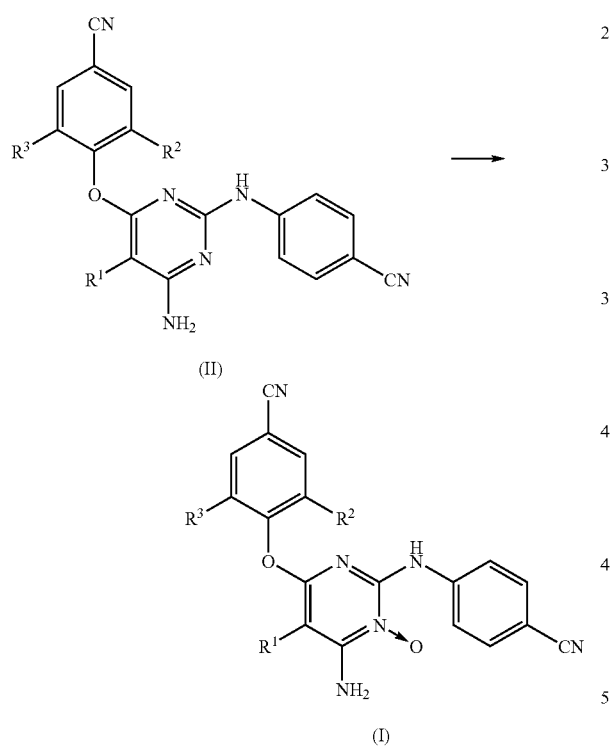

The N-oxidation reaction to prepare the compounds of formula (I) may be carried out by reacting the starting material of formula (II) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert.butyl hydro-peroxide. Preferred is 3-chlorobenzenecarbo-peroxoic acid (m-CPBA). The N-oxidation reaction usually is conducted in a suitable solvent such as, for example, water; a lower alcohol, e.g. ethanol and the like; a hydrocarbon, e.g. toluene; a ketone, e.g. acetone or 2-butanone; a halogenated hydro-carbon, e.g. dichloromethane or chlorophorm; and any mixtures of such solvents. Preferred are halogenated hydrocarbons, in particular dichloromethane. The end products may be purified using methods generally known in the art such as extraction, crystallization, trituration and chromatography.

The starting compounds of formula (II) are known compounds, which can be prepared according to procedures described in WO00/27825. They can be prepared by reacting an intermediate of formula (III) or (V) with an intermediate of formula (IV) or (VI), as outlined in the following reaction scheme, wherein $R^1$, $R^2$ and $R^3$ are as specified for the compounds of formula (I) or any subgroup thereof and W represents a suitable leaving group, such as for example halogen, e.g. chloro and the like.

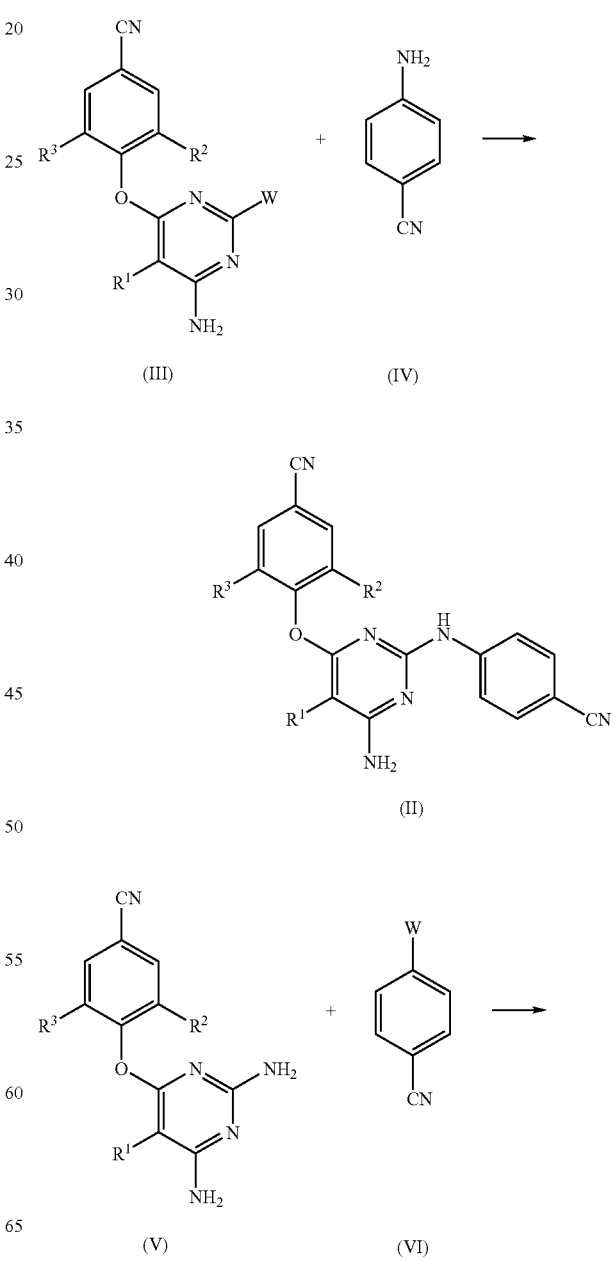

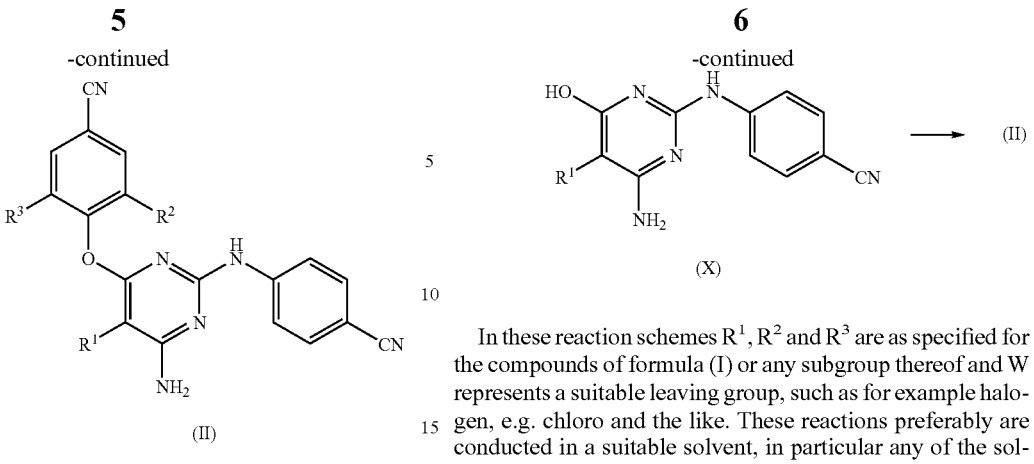

The reaction of the pyrimidine derivative (III) respectively (V) with the cyanoaniline (IV) respectively the cyanophenyl derivative (VI), is preferably conducted in a suitable solvent, such as for example an alcohol, such as for example methanol, ethanol, 2-propanol; N,N-dimethylformamide; N,N-dimethylacetamide, 1-methyl-2-pyrrolidinone; 1,4-dioxane, propylene glycol monomethylether; acetonitrile. The reactions may be done under acidic conditions which may be obtained by adding a suitable acid, e.g. camphor sulfonic acid, to a suitable solvent, such as for example tetrahydrofuran or an alcohol, e.g. ethanol, 1- or 2-propanol, or by using acidified solvents, e.g. hydrochloric acid dissolved in an alkanol such as ethanol, 1- or 2-propanol.

The compounds of formula (II) can also be prepared by reacting a cyanophenyl derivative (VII) with a pyrimidine derivative (VIII) or by reacting a cyanophenyl derivative (IX) with a pyrimidine derivative (X) as outlined in the following schemes.

In these reaction schemes $R^1$, $R^2$ and $R^3$ are as specified for the compounds of formula (I) or any subgroup thereof and W represents a suitable leaving group, such as for example halogen, e.g. chloro and the like. These reactions preferably are conducted in a suitable solvent, in particular any of the solvents mentioned above in relation to the reaction of (III) with (IV).

Still another way to prepare compounds of formula (II) is by halogenating a starting material (XI) with free halogen, e.g. free chlorine or bromine, or with a halogen donor such as N-bromo or N-chloro succinimide. This halogenation reaction preferably is conducted in a suitable reaction-inert solvent such as an ether, in particular in THF. N-bromo or N-chloro succinimide can be used in the presence of acetic acid.

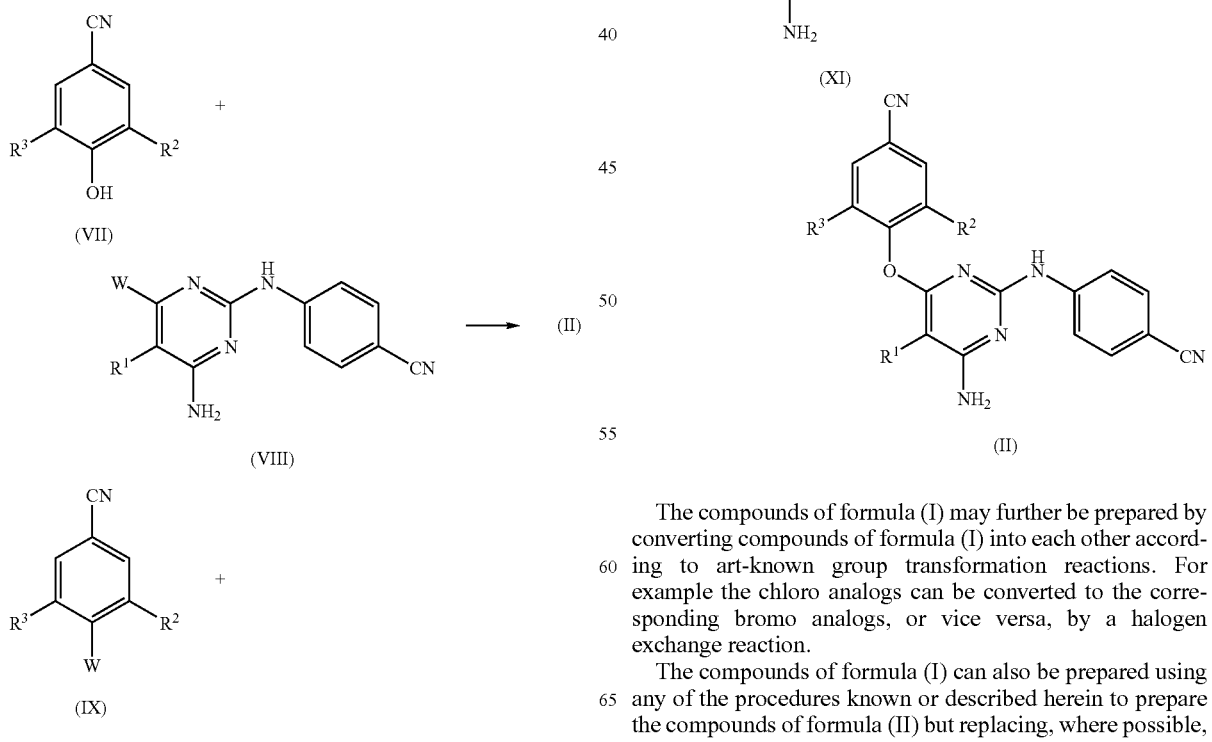

The compounds of formula (I) may further be prepared by converting compounds of formula (I) into each other according to art-known group transformation reactions. For example the chloro analogs can be converted to the corresponding bromo analogs, or vice versa, by a halogen exchange reaction.

The compounds of formula (I) can also be prepared using any of the procedures known or described herein to prepare the compounds of formula (II) but replacing, where possible, the pyrimidine starting materials by the corresponding pyrimidine oxides. The latter can be prepared by a similar N-oxidation reaction as described for the conversion of (II) into (I).

Some of the compounds of formula (I) and some of the precursor intermediates thereof may contain an asymmetric atom. Pure stereochemically isomeric forms of said compounds and said intermediates can be obtained by the application of art-known procedures.

The synthesis of some intermediates used in the previous reaction schemes is described hereinafter wherein in the following reaction schemes $R^1$, $R^2$ and $R^3$ are as specified for the compounds of formula (I) or any subgroup thereof and W represents a suitable leaving group, in particular chloro or bromo. The radical $R^1$ is halo but in the following reaction schemes it may also represent a precursor of a halo group such as hydroxy or a protected hydroxy (e.g. benzyloxy) which can be converted into a halo group by a halogenating agent such as POCl$_3$ or POBr$_3$. This may be preferred to avoid undesired side reactions.

Intermediates of formula (III) can be prepared by reacting a phenol derivative (XII) with a pyrimidine derivative (XIII) as outlined in the following reaction scheme.

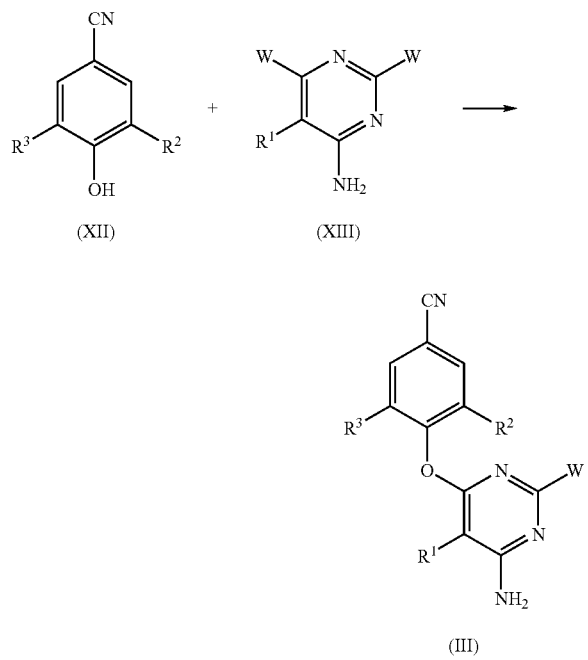

In a similar manner, intermediates (V) can be prepared starting from a pyrimidine (XV) as outlined in the following scheme:

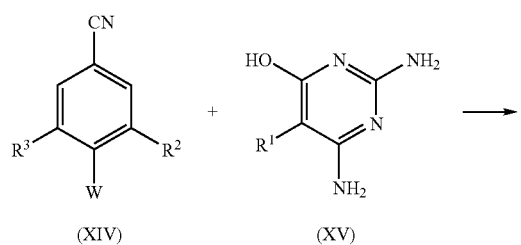

-continued

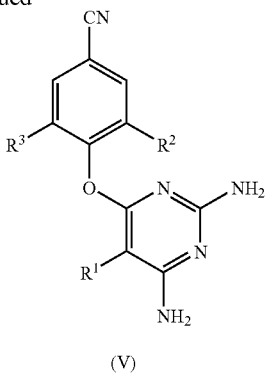

In the above reaction the amino group may or may not be protected by a suitable protective group.

Intermediates (X) can be prepared by condensing a pyrimidine derivative (XVI) with 4-aminobenzonitrile as outlined in the following scheme. If desired to avoid side reactions, the —OH and/or amino group may be protected and $R^1$ may be a precursor of halo as set forth above.

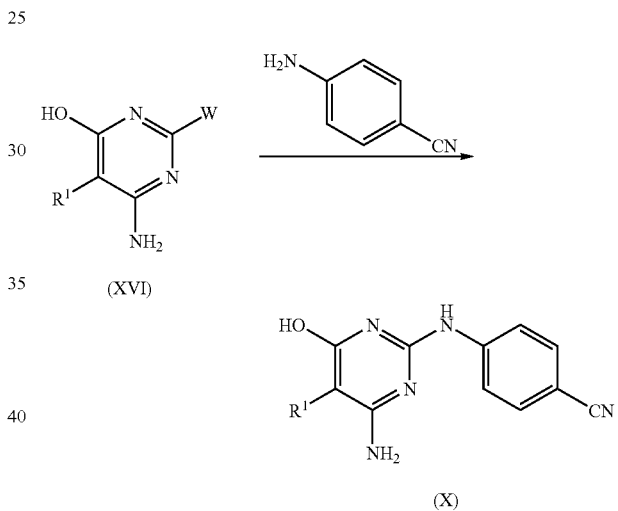

Intermediates of formula (XI) can be prepared as outlined in the reaction scheme represented here below. First 4-aminobenzonitrile is reacted with cyanamide to yield 4-cyanophenyl guanidine (XVII). This reaction may be conducted in water in the presence of a strong acid, e.g. hydrochloric acid, at increased temperature, e.g. at about 50° C. to 70° C., e.g. at about 60° C. The latter is reacted with a diC$_{1-6}$alkyl malonic ester of formula (XVIII), wherein each R independently is C$_{1-6}$alkyl, preferably each R is methyl. This reaction may be conducted in a suitable solvent, e.g. an alcohol such as methanol, in the presence of a strong base such as an alkali metal alkoxide, e.g. sodium methoxide, at increased temperature such as at reflux temperature. The thus obtained 4,6-dihydroxypyrimidine (XIX) is converted to a pyrimidine derivative (XX) wherein each W is a leaving group and in particular is halo, preferably chloro or bromo. This conversion can be done by using a suitable halogenating agent such as POCl$_3$ or POBr$_3$ in a suitable solvent, in particular a polar aprotic solvent, e.g. in DMF, DMA, HMPT, N-methylpyrrolidone, DMSO and the like, preferably in acetonitrile. Other leaving groups can be introduced following art-know alcohol to leaving group conversion reactions. The pyrimidine derivative (XX) is then reacted with a 4-substituted benzonitrile (XXI) to yield the desired intermediates (XXI). The reaction of (XX) with (XXI) may be conducted in a suitable solvent such as an ether, e.g. THF, a halogenated hydrocarbon, e.g. $CH_2Cl_2$, $CHCl_3$ and in particular a polar aprotic solvent, e.g. in DMF, DMA, HMPT, acetonitrile, DMSO and the like, and preferably in N-methyl-pyrrolidone. A base may be added to pick up the acid that is liberated during the course of the reaction, e.g. an alkali metal carbonate such as potassium carbonate.

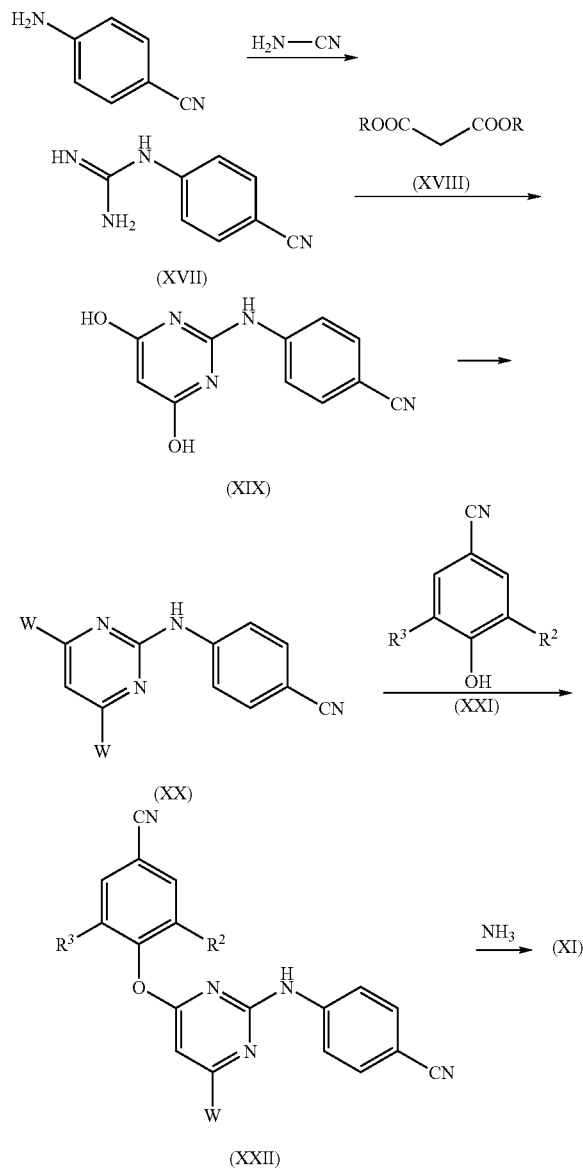

The compounds of formula (I) show antiretroviral properties (reverse transcriptase inhibiting properties), in particular they are active against HIV, which is the aetiological agent of Acquired Immune Deficiency Syndrome (AIDS) in humans. HIV preferentially infects human T-4 cells and destroys them or changes their normal function, particularly the coordination of the immune system. As a result, an infected patient has an ever-decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against mutated HIV strains, including as well single, double, triple or multiple mutated strains. The compounds of this invention are active against (multi) drug resistant HIV strains, in particular (multi) drug resistant HIV-1 strains, more in particular the present compounds show activity against HIV strains, especially HIV-1 strains that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and known to the person skilled in the art, in particular commercial non-nucleoside reverse transcriptase inhibitors. The present compounds may have little or no binding affinity to human α-1 acid glycoprotein; human α-1 acid glycoprotein may not or only weakly affect the anti HIV activity of the present compounds.

Due to their antiretroviral properties, in particular their anti-HIV properties, especially their anti-HIV-1-activity, the compounds of formula (I), the pharmaceutically acceptable addition salts and stereochemically isomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against abovementioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In a further aspect of this invention, there is provided a method of treating warm-blooded animals, including humans, suffering from, or a method of preventing warm-blooded animals, including humans, to suffer from viral infections, especially HIV infections. Said method comprises the administration, preferably oral administration, of an effective amount of a compound of formula (I), a pharmaceutically acceptable addition salt or a possible stereoisomeric form thereof, to warm-blooded animals, including humans.

In another aspect, the compounds of formula (I) or any subgroup thereof are useful in a method for preventing, treating or combating infection or disease associated with infection of a mammal with a mutant HIV virus, comprising administering to said mammal an effective amount of a compound of formula (I) or any subgroup thereof.

In another aspect, the compounds of formula (I) or any subgroup thereof are useful in a method for preventing, treating or combating infection or disease associated with infection of a mammal with a multi drug-resistant HIV virus, comprising administering to said mammal an effective amount of a compound of formula (I) or any subgroup thereof.

In yet another aspect, the compounds of formula (I) or any subgroup thereof are useful in a method for inhibiting replication of a HIV virus, in particular a HIV virus having a mutant HIV reverse transcriptase, more in particular a multi-drug resistant mutant HIV reverse transcriptase, comprising administering to a mammal in need thereof an effective amount of a compound of formula (I) or any subgroup thereof.

Preferably, a mammal as mentioned in the methods of this invention is a human being.

The present invention also provides compositions for treating viral infections comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy-$C_{1-6}$alkyl, particularly hydroxyethyl, hydroxy-propyl or hydroxybutyl; carboxy-$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated 1-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD). Another type of substituted cyclodextrins is sulfobutylcyclodextrines.

The term mixed ether denotes cyclodextrin derivatives wherein at least two cyclo-dextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "solid dispersion" used hereinafter defines a system in a solid state (as opposed to a liquid or gaseous state) comprising at least two components, in case the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered.

The term "solid dispersion" also comprises dispersions, which are less homogenous throughout than solid solutions. Such dispersions are not chemically and physically uniform throughout or comprise more than one phase, for example, systems having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation. After preparing the solid dispersions, the obtained products can be optionally milled and sieved. The solid dispersion product may be milled or ground to particles having a particle size of less than 600 µm, preferably less than 400 µm and most preferably less than 125 µm. The particles prepared as described hereinabove can then be formulated by conventional techniques into pharmaceutical dosage forms such as tablets and capsules.

The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkyl-celluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gum arabic, guar gum and xanthan gum, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water-soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are those described above as agents to aid solubility of the compounds of formula (I).

The ratio of the compound of formula (I) over the water-soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bind to said compound and may be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration. Such beads comprise a central, rounded or spherical core, a coating film of a hydrophilic polymer and a compound of formula (I) and optionally a seal-coating layer. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) can be used alone or in combination with other therapeutic agents, such as antivirals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in a single preparation together with pharmaceutically acceptable carriers. Said other antiretroviral compounds may be any known antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), D-D4FC (Reverset™), alovudine (MIV-310), amdoxovir (DAPD), elvucitabine (ACH-126,443), and the like; non-nucleoside reverse transcriptase inhibitors (NNRTIs) such as delarvidine (DLV), efavirenz (EFV), nevirapine (NVP), capravirine (CPV), calanolide A, TMC120, etravirine (TMC125), TMC278, BMS-561390, DPC-083 and the like; nucleotide reverse transcriptase inhibitors (NtRTIs), e.g. tenofovir (TDF) and tenofovir disoproxil fumarate, and the like; compounds of the TIBO (tetrahydroimidazo-[4,5,1-jk][1,4]-benzodiazepine-2(1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335; REV inhibitors; protease inhibitors e.g. ritonavir (RTV), saquinavir (SQV), lopinavir (ABT-378 or LPV), indinavir (IDV), amprenavir (VX-478), TMC-126, BMS-232632, VX-175, DMP-323, DMP-450 (Mozenavir), nelfinavir (AG-1343), atazanavir (BMS 232, 632), palinavir, TMC-114, RO033-4649, fosamprenavir (GW433908 or VX-175), P-1946, BMS 186,318, SC-55389a, L-756,423, tipranavir (PNU-140690), BILA 1096 BS, U-140690, and the like; entry inhibitors which comprise fusion inhibitors (e.g. T-20, T-1249), attachment inhibitors and co-receptor inhibitors; the latter comprise the CCR5 antagonists and CXR4 antagonists (e.g. AMD-3100); examples of entry inhibitors are enfuvirtide (ENF), GSK-873,140, PRO-542, SCH-417,690, TNX-355, maraviroc (UK-427,857); a maturation inhibitor for example is PA-457 (Panacos Pharmaceuticals); inhibitors of the viral integrase; ribonucleotide reductase inhibitors (cellular inhibitors), e.g. hydroxyurea and the like.

By administering the compounds of the present invention with other anti-viral agents, which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional anti-retroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithio-carbamate, tumor necrosis factor, naltrexone and the like; antibiotics, e.g. pentamidine isethiorate and the like; cholinergic agents, e.g. tacrine, rivastigmine, donepezil, galantamine and the like; NMDA channel blockers, e.g. memantine to prevent or combat infection and diseases or symptoms of diseases associated with HIV infections, such as AIDS and ARC, e.g. dementia. A compound of formula (I) can also be combined with another compound of formula (I).

Although the present invention focuses on the use of the present compounds for preventing or treating HIV infections, the present compounds may also be used as inhibitory agents for other viruses, which depend on similar reverse transcriptases for their reproduction.

The following examples are intended to illustrate the present invention and not to limit its scope thereto.

EXAMPLES

Example 1

Synthesis of 4-[[6-amino-5-bromo-2-[(4-cyanophenyl)amino]-4-pyrimidinyl]oxy]-3,5-dimethylbenzonitrile

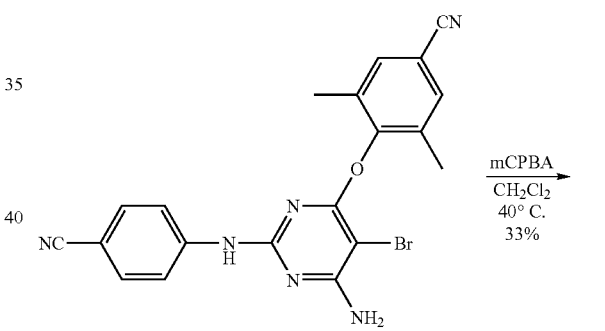

Intermediate 1

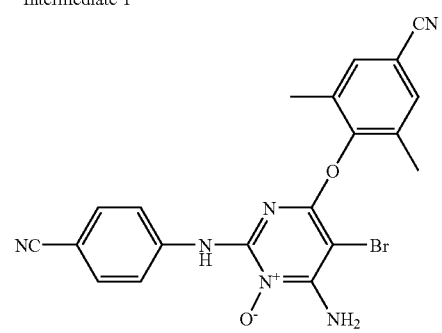

Compound 1

A mixture of 4-[[6-amino-5-bromo-2-[(4-cyanophenyl)amino]-4-pyrimidinyl]oxy]-3,5-dimethylbenzonitrile (Intermediate 1; 5.00 g, 11.5 mmol) and m-CPBA (3 equiv., 34.5 mmol, 8.50 g 70 wt %) was refluxed in dichloromethane (100 ml). After 10 minutes a clear solution was formed and 5 minutes later a precipitate formed. The mixture was refluxed for an additional 15 minutes, cooled to room temperature and the white solid was filtered and rinsed with dichloromethane. The solid was stirred in acetic acid for 1 hour, filtered and dried to give 1.7 g (33%) of Compound 1.

Physical data: mp. 271° C. (AcOH),
$^1$H NMR (300 MHz, DMSO) δ 1.90 (s, 2.25H, AcOH), 2.12 (s, 6H), 7.39 (d, 2H), 7.40 (d, 2H), 7.76 (s, 2H), 7.95 (br s, 2H), 10.2 (br s, 1H). The product contains 0.75 equivalents of acetic acid.

LCMS analysis (1 ml/min linear gradient to 95% 10 mM aqueous HCOOH/acetonitrile to $t_{15}$ 5% 10 mM aqueous HCOOH/acetonitrile, UV-DAD): 95% pure, t=9.49 min, mass spectrum m/z 449, 451 [M-H]$^-$.

Example 2

Formulations

Capsules

Compound 1 as described in example 1, is dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxypropylmethylcellulose (HPMC), typically 5 mPa·s, are dissolved in organic solvents such as ethanol, methanol methylene chloride. Suitably the polymer is dissolved in ethanol. The polymer and compound solutions are mixed and subsequently spray dried. The ratio of compound/polymer is selected from 1/1 to 1/6. Intermediate ranges can be 1/1.5 and 1/3. A suitable ratio can be 1/6. The spray-dried powder, a solid dispersion, is subsequently filled in capsules for administration. The drug load in one capsule ranges between 50 and 100 mg depending on the capsule size used.

Film-Coated Tablets
Preparation of Tablet Core

A mixture of 100 g of a compound 1, 570 g lactose and 200 g starch are mixed well and thereafter humidified with a solution of 5 g sodium dodecyl sulfate and 10 g polyvinylpyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methylcellulose in 75 ml of denaturated ethanol there is added a solution of 5 g of ethylcellulose in 150 ml of dichloromethane. Then there is added 75 ml of dichloromethane and 2.5 ml 1,2,3-propanetriol. 10 g of polyethylene glycol is molten and dissolved in 75 ml of dichloromethane. The latter solution is added to the former and then there is added 2.5 g of magnesium octadecanoate, 5 g of polyvinyl-pyrrolidone and 30 ml of concentrated color suspension and the whole is homogenated. The tablet cores are coated with the thus obtained mixture in a coating apparatus.

Example 3

Antiviral Spectrum

Because of the increasing emergence of drug resistant HIV strains, the present compounds were tested for their potency against clinically isolated HIV strains harboring several mutations. These mutations are associated with resistance to reverse transcriptase inhibitors and result in viruses that show various degrees of phenotypic cross-resistance to the currently commercially available drugs such as for instance AZT and delavirdine.

The antiviral activity of the compound of the present invention is evaluated in the presence of wild type HIV and HIV mutants bearing mutations at the reverse transcriptase gene. The activity of the compounds is evaluated using a cellular assay and the residual activity is expressed in pEC$_{50}$ values. The columns IIIB and A-G in the table list the pEC$_{50}$ values against various strains IIIB, A-G.

Strain IIIB is wild type HIV-LAI strain;
Strain A contains mutation Y181C in HIV reverse transcriptase,
Strain B contains mutation K103N in HIV reverse transcriptase,
Strain C contains mutation L100I in HIV reverse transcriptase,
Strain D contains mutation Y188L and S162K in HIV reverse transcriptase,
Strain E contains mutations L100I and K103N in HIV reverse transcriptase,
Strain F contains mutations K101E and K103N in HIV reverse transcriptase.

| Compound number | IIIB | A | B | C | D | E | F |
|---|---|---|---|---|---|---|---|
| 1 | 9.24 | 9.20 | 8.85 | 9.20 | 9.22 | 8.97 | 8.98 |
| A | 8.55 | 8.00 | 8.75 | 8.54 | 8.61 | 8.09 | 8.34 |

Compound A is a reference compound and is the compound referred to as 'Intermediate 1' in example 1 and has been described in WO-00/27825.

The invention claimed is:
1. A compound of formula

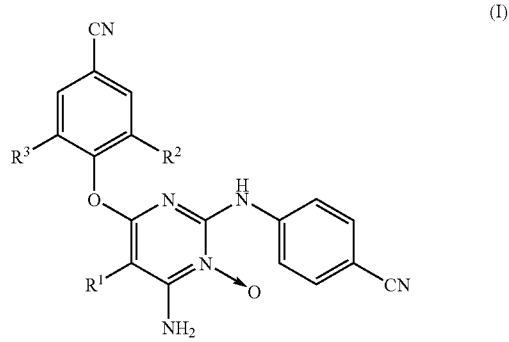

(I)

or a pharmaceutically acceptable addition salt thereof, wherein
R$^1$ is bromo;
R$^2$ and R$^3$ are methyl.
2. A pharmaceutical composition comprising a pharmaceutically acceptable carrier and as active ingredient a therapeutically effective amount of a compound as claimed in claim 1.
3. A process for preparing a composition according to claim 2, the process comprising intimately mixing the active ingredient and the carrier.

* * * * *